(12) United States Patent
Wesson (10) Patent No.: US 6,203,214 B1
(45) Date of Patent: Mar. 20, 2001

(54) ALIGNMENT SYSTEM FOR SPLICING OF POLARIZATION-MAINTAINING SINGLE MODE OPTICAL FIBER

(76) Inventor: Laurence N. Wesson, 625 Cranstone La., Blue Bell, PA (US) 19422

( * ) Notice: Subject to any disclaimer, the term of this patent is extended or adjusted under 35 U.S.C. 154(b) by 0 days.

(21) Appl. No.: 09/244,276

(22) Filed: Feb. 3, 1999

Related U.S. Application Data (63) Continuation-in-part of application No. 08/780,697, filed on Jan. 8, 1997, now abandoned, which is a continuation-in-part of application No. 08/816,991, filed on Mar. 13, 1997, now abandoned, which is a continuation of application No. 08/439,255, filed on Mar. 11, 1995, now abandoned, which is a continuation-in-part of application No. 08/115,734, filed on Sep. 1, 1993, now Pat. No. 5,417,333.

(51) Int. Cl.[7] .................................................. G02B 6/38
(52) U.S. Cl. .................. 385/97; 65/378; 65/407; 65/485; 65/501; 65/29.12; 385/98; 385/147

(58) Field of Search ................................ 385/147, 97, 98; 65/406, 407, 378, 485, 501, 29.12, 160

(56) References Cited

U.S. PATENT DOCUMENTS

| 5,011,259 | * | 4/1991 | Lieber et al. | 350/96.21 |
| 5,131,745 | * | 7/1992 | Whitney | 385/25 |
| 6,046,798 | * | 4/2000 | Zamzow | 356/73.1 |

* cited by examiner

Primary Examiner—Hung N. Ngo
(74) Attorney, Agent, or Firm—Ernest D. Buff & Associates; Ernest D. Buff (57) ABSTRACT

Asymmetric stress in the tip of a polarization-maintaining optical fiber is measured using the photoelastic effect to determine the fiber polarization axes of two fibers appointed to be joined. The fibers are rotated to align their respective polarization axes and are joined together. A single polarization-maintaining optical fiber is thereby produced in an accurate, reliable, time efficient and cost effective manner.

6 Claims, 7 Drawing Sheets

ALIGNMENT SYSTEM FOR SPLICING OF POLARIZATION-MAINTAINING SINGLE MODE OPTICAL FIBER

CROSS REFERENCE TO RELATED APPLICATION

This application is a CIP of Ser. No. 08/780,697 Jan. 8, 1997 ABN which is a continuation-in-part of application Ser. No. 08/816,991, filed Mar. 13, 1997, abandoned which, in turn, is a file-wrapper continuation of application Ser. No. 08/439,255, filed Mar. 11, 1995 now abandoned which, in turn, is a continuation-in-part of Ser. No. 08/115,734, filed Sep. 1, 1993 entitled "Alignment System For Splicing Of Polarization-Maintaining Single Mode Optical Fiber", now U.S. Pat. No. 5,417,333.

BACKGROUND OF THE INVENTION

1. Field of the Invention

The present invention relates to a fully automatic passive rotational alignment system for the splicing of polarization-maintaining single mode fiber.

2. Description of the Prior Art

Polarization-maintaining single mode fibers present special difficulty in splicing or coupling. Ordinary single mode fibers must be aligned with each other laterally and longitudinally to within about 1 micron, and in angle to within a fraction of a degree. Polarization-maintaining fibers must also be aligned azimuthally; that is, they must be rotated relative to each other about their common axis until the fast and slow axes in their respective cores are also aligned. This is because it is essential for the successful application of these fibers that the transmitted light remain in the preferred polarized mode—either fast or slow—in crossing the splice. If the mode alignment is off by more than about 1 degree very serious losses take place. Not only does the projected power become divided between the two orthogonal modes of the receiving fiber, but the coupling into the originally-excited mode is very poor. An effective means of aligning such fibers is thus clearly desirable.

In U.S. Pat. No. 4,612,028, there is disclosed a polarization-preserving single mode fiber coupler made without mutually aligning the polarization axes of the fibers by twisting the fibers together over a selected length and fusing them. A critical requirement of this coupling method is that the initial misalignment be not close to 90 degrees.

As taught in U.S. Pat. Nos. 5,156,663 and 4,911,524, the principal manner of aligning polarization maintaining single mode fibers has heretofore been to rotate a first fiber relative to a second fiber while exciting the first fiber and monitoring the output from the second. That is, the first "transmitting" fiber must be aligned with a polarized light source for injection of light aligned with the preferred axis. Likewise, the output end of the "receiving" fiber must have its preferred axis aligned with a polarizing filter and detector. Thereafter, the ends of the fibers to be spliced or coupled are brought together in a suitable stage or housing, for instance on a fusion splicer. After the ends have been aligned laterally with each other in x, y, and z dimensions, to maximize the coupling of power across the gap, one fiber is rotated slowly relative to the other while the power received at the photodetector is monitored. Eventually an orientation is found at which the coupling of power into the preferred axis is optimum. The fusion or mechanical splice is then completed, by fixing the oriented ends together permanently.

U.S. Pat. No. 5,244,977 to Anjan, et al. discloses a fiber optic polarization apparatus for use in the fabrication of fused optical couplers. U.S. Pat. No. 5,013,345 to Itoh, et al. discloses a method for fusion splicing of polarization maintaining optical fibers, while U.S. Pat. No. 5,149,350 to Itoh, et al. discloses an apparatus for fusion splicing of optical fibers. In each of these systems, light is injected into a free end of one fiber and detected at a free end of the second fiber. The fibers are aligned by monitoring the light transmitted through the joining surfaces as a function of angle.

U.S. Pat. No. 4,669,814 to Dyott discloses an optical fiber comprising a core and cladding having different refractive indices and forming a single-mode guiding region, where the core has a noncircular cross-section defining two refractive indices. Like the Anjan, et al. and Itoh, et al. systems, the Dyott system discloses a fiber in which light is injected along its length. The injection of light in the Dyott system is accomplished by a beam splitter.

Coupling of fibers using the methods described hereinabove require light to be injected along the length of the joining fibers. Rotational alignment is, alternatively, accomplished by the following methods: (1) coupled power monitoring, which is difficult and time consuming, and requires expensive input and output source and detector alignments; (2) axial imaging, which requires the fiber to have obvious and distinctive features; and (3) lateral imaging, in which the fiber must have obvious internal features amenable to a precisely-alignable image. With the first (power injection/detection) fiber alignment method, the set-up required to power and monitor the fibers is difficult and time-consuming to establish. Highly-skilled personnel are required; and the splicing procedure is itself time-consuming. If more than one pair of fibers is to be spliced, the process time and procedural difficulty increase dramatically. Methods (2) and (3) depend on imaging distinctive internal physical features of the fibers. If alignment is to be automatic, the system therefore requires sophisticated, expensive, and delicate image processing technology. If it is to be manual, the ability of a user to visually match two low-contrast images is oftentimes not accurate enough to yield rotational alignments of the required precision of 1 degree or better. Furthermore, few pm fibers exhibit images with distinguishable features, either in the axial or lateral views. Thus methods (2) and (3) are both difficult to implement and limited in applicability to a small proportion of the available pm fibers.

There remains a need in the art for an improved method for coupling polarization-maintaining single mode fibers.

SUMMARY OF THE INVENTION

The present invention provides a method and means for joining two separate polarization-maintaining optical fibers into a single polarization-maintaining optical fiber by use of transverse illumination. Asymmetric stress in the tip of a polarization-maintaining optical fiber is measured using the photoelastic effect to determine the fiber polarization axes of two fibers appointed to be joined. The fibers are rotated around their longitudinal axis to align their respective polarization axes and joined together. In this manner, a single polarization-maintaining optical fiber is produced.

Generally stated, the invention provides an automatable apparatus for aligning the polarizations of two single mode optical fibers, comprising: a first measuring means for measuring a first transverse intensity function of a first optical fiber; a second measuring means for measuring a second transverse intensity function of a second optical fiber; a first rotation means for rotating the first optical fiber about an axis through the length of the first optical fiber; a second rotation means for rotating the second optical fiber about an axis through the length of the second optical fiber; a lateral alignment means for laterally aligning a first end surface of the first optical fiber with a second end surface of the second optical fiber, whereby the first end surface and the second end surface are coincident, or laterally aligned, forming a boundary between the first optical fiber and the second optical fiber; a memory means for storing the first transverse intensity function and the second transverse intensity function; a microprocessor means for controlling the first rotation means and the second rotation means, the microprocessor means being operative to identify first fiber polarization axes from the first transverse intensity function, second fiber polarization axes from the second transverse intensity function, and the angular difference between the first fiber polarization axes and second fiber polarization axes; and a software means for directing the microprocessor means to cause the first rotating means to rotate the first optical fiber until the first polarization axes and the second polarization axes are aligned.

In one aspect of the invention, there is provided an apparatus for aligning two optical fibers, comprising: illumination means for projecting polarized light transversely through first and second optical fibers having discrete lengths and observable, internal asymmetric stress; polarized light detection means for receiving the light passed transversely through said fibers and producing therefrom an electrically detected signal; measuring means for creating first and second transverse intensity functions from variations in said electrically detected signal as said first and second optical fibers are rotated; rotation means for rotating each of said first and second optical fibers about an axis through the lengths of said fibers; and alignment means for laterally aligning a first end surface of said first optical fiber with a second end surface of said second optical fiber, whereby said first end surface and said second end surface are coincident and form a boundary between said first optical fiber and said second optical fiber.

In another aspect, there is provided an apparatus for identifying the polarization axis of an optical fiber, comprising: illumination means for projecting polarized light transversely through said optical fiber, said optical fiber having a discrete length and observable, internal asymmetric stress; polarized light detection means for receiving the light passed transversely through said fiber and producing therefrom an electrically detected signal; measuring means for creating a transverse intensity function of said optical fiber from variation in said electrically detected signal as said optical fiber is rotated; and rotation means for rotating said optical fiber about an axis through its length to characterize said transverse intensity function and correlate it with a feature of said fiber.

The invention further provides a method for aligning the optical polarization of two single mode optical fibers, comprising the steps of: placing a first end surface of a first optical fiber against a second end surface of a second optical fiber, whereby the first end surface and the second end surface are coincident, or laterally aligned, forming a boundary between the first optical fiber and the second optical fiber; transversely illuminating an end of the first optical fiber with a first polarized light having a first polarization direction; rotating the first optical fiber about an axis through the length of the first optical fiber; filtering the first polarized light with a first polarizing filter having a polarization axis oriented to the first polarization direction; detecting the first polarized light traversing the first optical fiber; recording the transverse intensity function of the first optical fiber; identifying first polarization axes from the first transverse function; transversely illuminating an end of the second optical fiber with a second polarized light; rotating the second optical fiber about an axis through the length of the second optical fiber; filtering the second polarized light with a second polarizing filter having a polarization axis oriented to the second polarization direction; detecting the second polarized light traversing the second optical fiber; recording the transverse intensity function of the second optical fiber; identifying second polarization axes from the second transverse intensity function; determining the angular difference between the first polarization axes and the second polarization axes; and aligning the first polarization axes and the second polarization axes, whereby the first optical fiber and the second optical fiber maintain orientation of polarization across the boundary.

The method and apparatus of the present invention afford significant advantages over previous alignment systems. Inasmuch as the fibers appointed for alignment need not be coupled at their far ends to source and detector, the alignment set-up procedure is less complex. Coupling is readily effected in an accurate, reliable manner without need of skilled personnel, and the time and cost required for splicing polarization-maintaining single mode fiber is reduced.

In practice, fiber alignment is accomplished without need of visually observable fiber features. Fiber imaging is unnecessary and is not is not used in operation of the apparatus. Polarization is inferred from the internal stress field, which may arise from means other than distinct internal components (as, for instance, an elliptical cladding dopant gradient). Image-forming systems, such as CCD cameras, and the associated image-processing computer systems are eliminated. Operational cost, efficiency and reliability are increased and splicing time is decreased. Less time is spent waiting for fibers to be aligned, and many more fibers are aligned each day.

BRIEF DESCRIPTION OF THE DRAWINGS

The invention will be more fully understood and further advantages will become apparent when reference is made to the following detailed description of the preferred embodiment of the invention and the accompanying drawings, in which.

DESCRIPTION OF THE PREFERRED EMBODIMENTS

Polarization-maintaining fibers exhibit asymmetric stresses. In most such fibers the stresses are created deliberately, as the decoupling of the two degenerate polarized modes is achieved by refractive index changes due to stress. The unequal stresses result in very different propagation constants for the two orthogonal modes, which reduce cross-coupling to a very low level, typically −20 to −30 dB. The asymmetric stresses are achieved by the use of an elliptical inner cladding layer (3M and Hitachi), a bow-tie-shaped pair of regions (York), a pair of rods (Panda), or some other internal glass structure with a thermal expansion coefficient different from that of the fiber core and the rest of the cylindrical fiber cladding.

Other fibers, such as those made by Andrew and Corning, are "form birefringent." In these cases, the core may be elliptical so as to impose different propagation constants on the two modes. Even though asymmetric stress is not imposed deliberately, it can be expected that since there are different coefficients of thermal expansion in the various fiber layers, form asymmetry leads automatically and unavoidably to stress asymmetry. Although the stress levels may be lower than in stress-birefringent fibers, they are still detectable.

Figure 1:
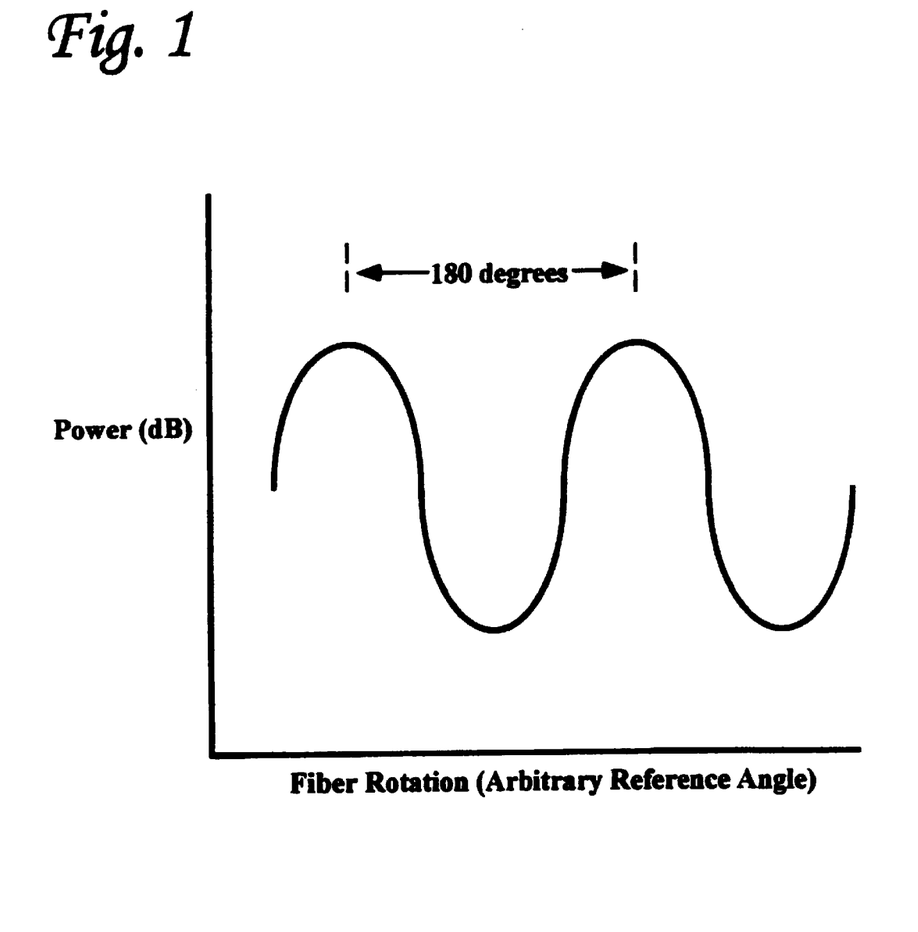
FIG. 1 is a schematic of a typical transverse intensity function.

When an illumination means is used to project polarized light through the fiber transversely or perpendicular to the fiber's length, the stresses in the fiber introduce phase delays in the light according to the photoelastic effect. When the transmitted polarized light is allowed to fall on a polarized light detection means for receiving the light passed transversely through the fiber, the amount of light which reaches the detector varies with the fiber's rotation. That is, as the stressed region of the fiber is rotated relative to the transverse polarized light, the phase delay it creates in the light varies, changing the polarization state of the light. When the altered polarized light falls on a polarized detection means, the amount of light which can pass through to be detected and converted to an electrical signal varies. Rotation of the fiber results in variation of the detector signal. This variation of the detector signal resulting from transverse light modulation is hereinafter referred to as a transverse intensity function. The transverse intensity function is easily amplified electronically and correlated with the orientation of the fiber. FIG. 1 is a schematic representation of a typical transverse intensity function, where the features are related to the fiber's polarization axes.

In the case of fiber made by Hitachi, the relative phase delay between two components of the polarized beam is estimated to reach a maximum of 0.68 radian when the direction of the transverse illumination is parallel to the long axis of the ellipse and 0.27 radian when it is along the short axis. This indicates that the phase delays to be expected will be single-order and usually much less than $\pi/2$; thus they will be unambiguous, and only a single peak will be expected to occur in the transverse intensity function for each 180 degrees of fiber rotation.

Figure 2:
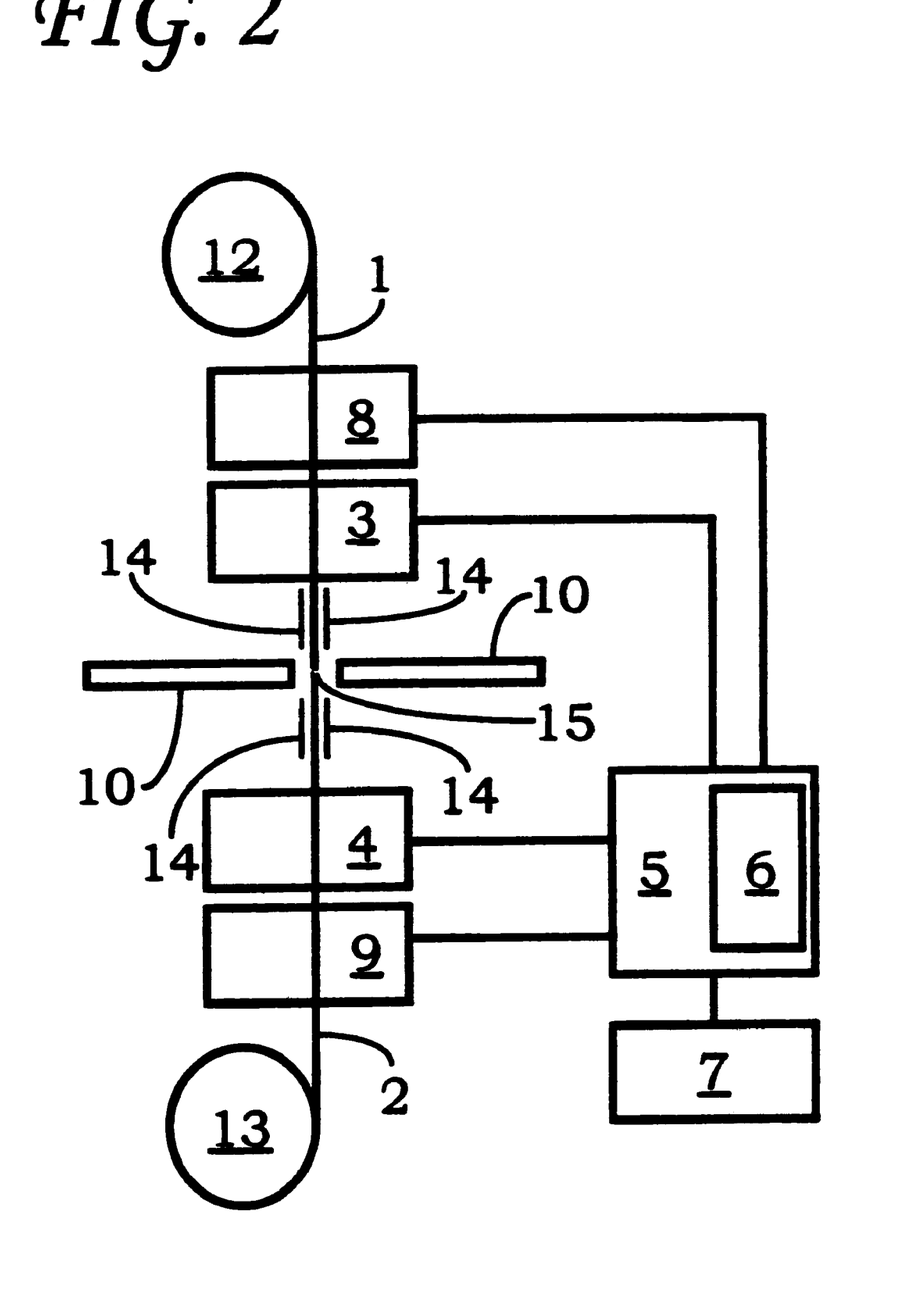
FIG. 2 is a schematic of the alignment system of the present invention.
Figure 3:
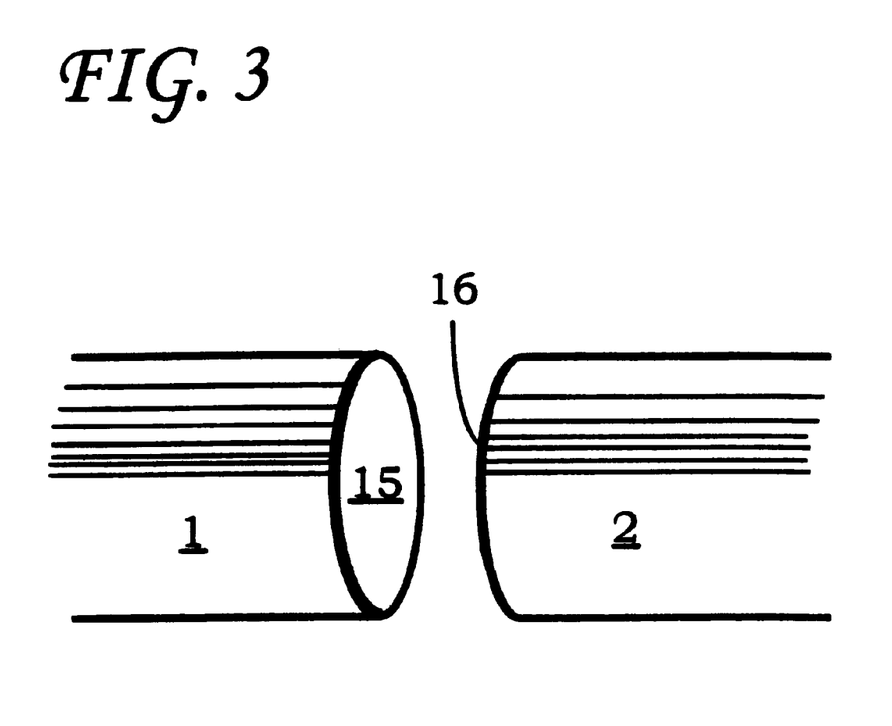
FIG. 3 is a perspective view of two fiber ends.

As shown in FIGS. 2 and 3, the apparatus comprises a first polarized light detection means 3 for obtaining a first transverse intensity function of a first optical fiber 1 from spool 12. First rotation means 8 rotates a first optical fiber 1 about an axis through the length of first optical fiber 1. Microprocessor means 5, under control of software means 6, directs first rotation means 8 to rotate first optical fiber 1. First polarized light detection means 3 measures the transverse intensity which is logged and related to the rotation angle of rotation means 8 is collected by microprocessor means 5 and stored in memory means 7.

Similarly, a second polarized light detection means 4 measures a second received transverse intensity function of a second optical fiber 2 from spool 13. Second rotation means 9 rotates second optical fiber 2 about an axis through the length of second optical fiber 2. Microprocessor means 5, under control of software means 6, directs second rotation means 9 to rotate second optical fiber 2. Second measuring means 4 measures the second received transverse intensity which, in turn, is collected by microprocessor means 5, correlated with the rotation angle of rotation means 9, and stored in memory means 7.

Alignment means 14 temporarily holds first optical fiber 1 and second optical fiber 2 into lateral alignment. The free end of first optical fiber 1 and the free end of second optical fiber 2 are butted against each other such that the first end surface 15 of the first optical fiber 1 and the second end surface 16 of the second optical fiber 2 are coincident, or laterally aligned, forming a boundary 15 between the first optical fiber 1 and the second optical fiber 2. The joining means 10 joins first optical fiber 1 at first end surface 15 to second optical fiber 2 at second end surface 16. The joining means 10 is a member of the group consisting of arc discharge, microflame, filament, glue (for instance, epoxy) in a capillary, mechanical clamping in a common V groove, and laser. Optionally, optical fiber 1 and optical fiber 2 are separated by a short gap and their free ends are fire polished to remove defects, before they are butted together while the joining means 10 is applied.

Figure 4:
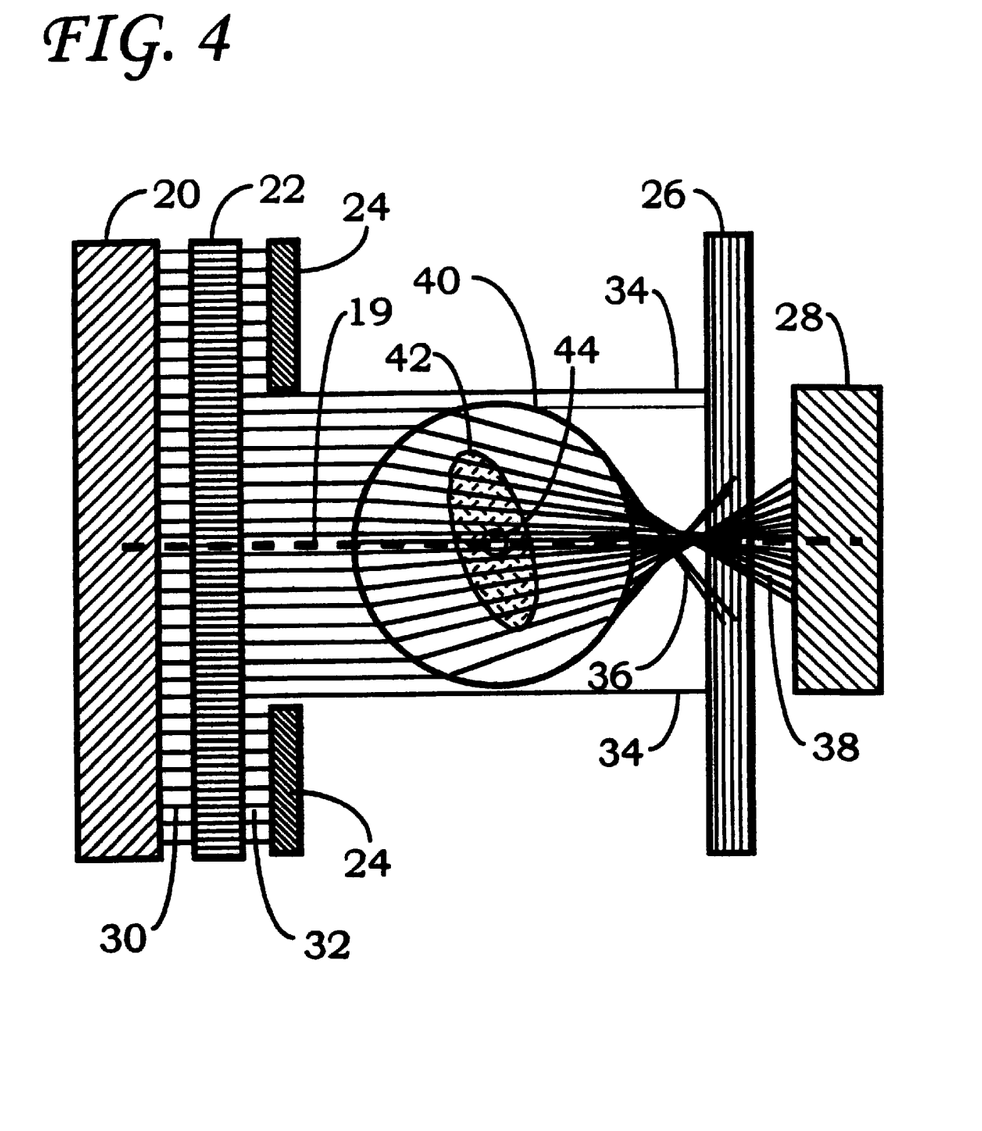
FIG. 4 shows a cross-sectional view of a first polarization-maintaining optical fiber transversely illuminated with polarized light.

In FIG. 4, the alignment system of FIG. 2 is shown in greater detail. Illumination means 20 generates a first light 30 along first light path 19. Illumination means 20 is a member of the group consisting of laser, laser diode, incandescent bulb, LED, and quartz lamp. A first light polarizing means 22 causes the first light 30 to become first polarized light 32, having a first polarization direction. The aperture 24 limits the area of first polarized light 32 to illuminate first optical fiber 40. The first polarized light 32 transversely illuminates the first optical fiber 40 (perpendicular to its length). For illustrative purposes, first optical fiber 40 is shown with an elliptical clad 42 and core 44. The first polarized light 32 entering first optical fiber 40 undergoes a change in polarization depending on the stresses in its path through the fiber. The light continues along the first light path 19, and in turn, impinges upon a second polarizing means 26. The second polarizing means 26 has a second polarization axis perpendicular to the first polarization direction of the first polarized light 32. The condition of the second polarizing filter 26 being 180 degrees out of phase with the first polarized light 32, the second polarizing means 26 rejects or filters light that does not traverse the fiber 40, shown in FIG. 4 as 34 and 36. Light that does traverse the stressed region 42 is altered in polarization state depending on the stress effects integrated over the path. Depending on the final polarization state of any ray of the light, some portion thereof, shown in the FIG. 4 as 38, will pass through the second polarizing filter 26 to be detected by first light detection means 28. First light detection means 28 is a member of the group consisting of photo-transistor, silicon detector, photo-diode, photo-resistor, photo-cell, and PIN detector. Optionally, focusing optics are positioned along first light path 19, for instance between the first optical fiber 1 and the first light detector 28.

Figure 5:
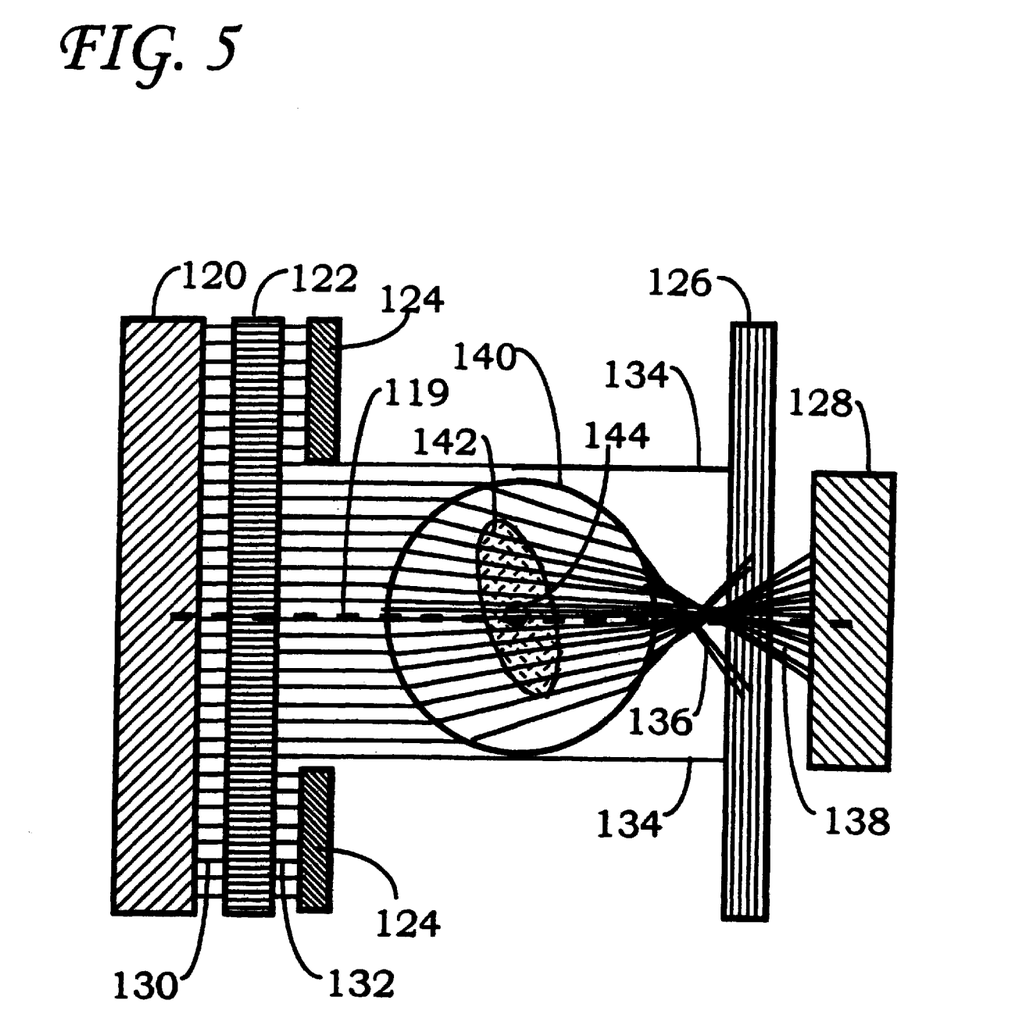
FIG. 5 shows a cross-sectional view of a second polarization-maintaining optical fiber transversely illuminated with polarized light.

Similarly, as shown in FIG. 5, illumination means 120 generates a second light 130 along second light path 119. Illumination means 120 is a member of the group consisting of laser, laser diode, incandescent bulb, LED, and quartz lamp. A second light polarizing means 122 causes the second light 130 to become second polarized light 132, having a second polarization direction. The aperture 124 limits the area of second polarized light 132 to illuminate second optical fiber 140. The second polarized light 132 transversely illuminates the second optical fiber 140 (perpendicular to its length). For illustrative purposes, second optical fiber 140 is shown with an elliptical clad 142 and core 144. The second polarized light 132 entering second optical fiber 140 undergoes a change in polarization depending on the stresses in its path through the fiber. The light continues along the second light path 119 and in turn falls upon a second polarizing means 126. The second polarizing means 126 has a second polarization axis perpendicular to the second polarization direction of the second polarized light 132. The condition of the second polarizing filter 126 being 180 degrees out of phase with the second polarized light 132 the second polarizing means 126 rejects or filters light that does not traverse fiber 140, shown in FIG. 5 as 134 and 136. Light that does traverse the stressed region is altered in polarization state depending on the stress effects integrated over the path. Depending on the final polarization state of any ray of the light, some portion thereof, shown in FIG. 5 as 138, will pass through the second polarizing filter 126 to be detected by second light detection means 128. Second light detection means 128 is a member of the group consisting of photo-transistor, silicon detector, photo-diode, photo-resistor, photo-cell, and PIN detector. Optionally, focusing optics are positioned along second light path 119, for instance between the second optical fiber 140 and the second light detector 128.

Figure 6:
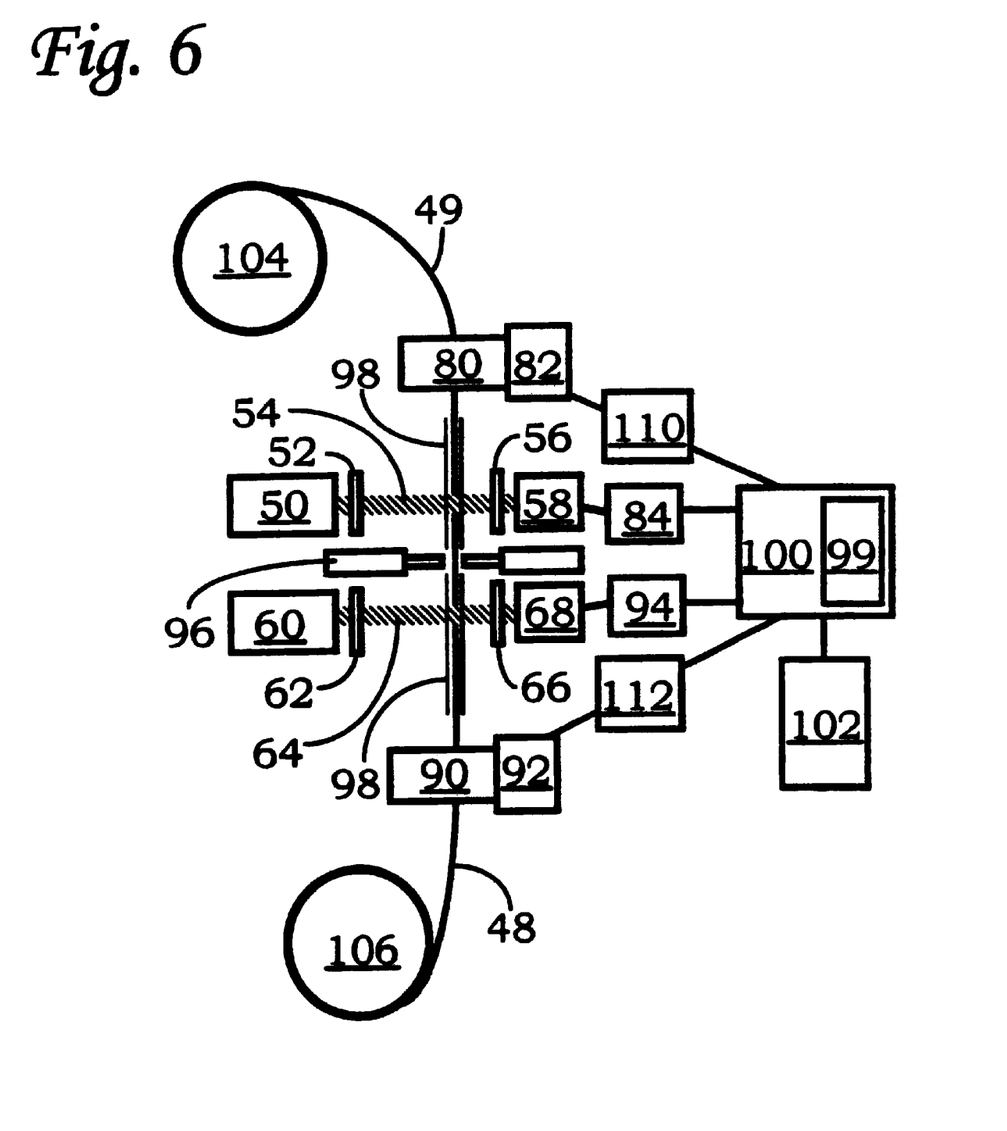
FIG. 6 is a detailed schematic of the alignment system shown in FIG. 2.

As shown in FIG. 6, two polarization-maintaining single mode fibers 48 and 49 appointed to be spliced are stripped and cleaved to length. The two fibers may be aligned laterally by ferrules 98. First optical fiber 49 is placed on a first rotating means comprised of a rotation stage 80 driven by stepper motor 82. A first rotation control means controls the rotation of first fiber 48. Preferably, the first rotation control means comprises software means 99. The software means 99 directs the microprocessor means 100 to send angle data, as digital commands, to stepper motor 82 via digital-to-analog converter 110. The tip of first optical fiber 49 extends beyond the rotation stage 80 where a first polarized light 54 is projected through the first optical fiber 49 laterally. First polarized light 54 is generated by an illumination means 50, such as an LED or laser diode, in conjunction with a polarizing filter 52. A first light detection means comprises a photodetector 58 and an analog-to-digital converter 84. The photodetector 58 receives the light focused through the first optical fiber 49 after traversing polarizing filter 56, making it a polarized light detection means. Further, a first correlating means creates a first transverse intensity function from the output of the polarized light detection means and the rotation angle of the rotating means. The microprocessor means 100 receives the output of photodetector 58 via analog-to-digital converter 84 and stores the photodetector data and corresponding angle data in memory 102. The software means 99 correlates the stored photodetector data with the stored angle data, generating a first transverse intensity function. In addition, the software means determines the first fiber polarization axes by analyzing the form of the first transverse intensity function.

Similarly, the second optical fiber 48 is placed on a second rotating means comprised of a rotation stage 90 driven by stepper motor 92. A second rotation control means controls the rotation of second fiber 49. Preferably, the second rotation control means comprises software means 99. The software means 99 directs the microprocessor means 100 to send angle data, as digital commands, to stepper motor 92 via digital-to-analog converter 112. The tip of second optical fiber 48 extends beyond the rotation stage 90 where a second polarized light 64 is projected through the second optical fiber 48 laterally. The second polarized light 64 is generated by an illumination means, such as an LED or laser diode, in conjunction with a polarizing filter 62. A second light detection means comprises a photodetector 68 and analog-to-digital converter 94. The photodetector 68 receives the light focused through the second optical fiber 48 after traversing a second polarizing filter 66. The microprocessor means 100 receives the output of photodetector 68 via analog-to-digital converter 94 and stores the photodetector data and corresponding angle data in memory 102. Further, a second correlating means creates a second transverse intensity function from the output of the second polarized light detection means and the rotation angle of the rotating means. The microprocessor means 100 under the direction of the software means 99 correlates the stored photodetector data with the stored angle data, generating a second transverse intensity function, and determines the second fiber polarization axes by analyzing the form of the second transverse intensity function.

The software means 99 directs the microprocessor means 100 to calculate the difference between the first fiber polarization axes and the fiber second polarization axes, and in turn, command stepper motor 82 via digital-to-analog converter 110 to cause rotation stage 80 to rotate first optical fiber 49 to align the first polarization axes with the second polarization axes. With the two fibers aligned laterally and polarization axes parallel, the final splicing step is carried out.

In practice, when aligning the optical polarization of two single mode polarization-maintaining optical fibers, the first end surface of a first optical fiber is placed close to the second end surface of a second optical fiber, whereby the first end surface and the second end surface are coincident or laterally aligned, forming a boundary between the two optical fibers. The first optical fiber is then transversely illuminated at one end with a first plane polarized light, while being rotated about an axis through its length. After traversing the first optical fiber, the first plane polarized light is filtered with a first plane polarizing filter having a polarization axis 90 degrees to the polarization direction of the first plane polarized light. The filtered first polarized light is then detected. The first transverse intensity function is recorded and the first polarization axes are determined. The second optical fiber is transversely illuminated at one end with a second plane polarized light, while rotated about an axis through its length. After traversing the second optical fiber, the second plane polarized light is filtered with a second plane polarizing filter having a polarization axis 90 degrees to the polarization direction of the second plane polarized light. The filtered second plane polarized light is then detected. The second transverse intensity function is recorded and the second polarization axes are determined. Next the angular difference between the first polarization axes and the second polarization axes is determined. The first polarization axes and the second polarization axes are then aligned to parallel, whereby the first optical fiber and the second optical fiber maintain orientation of polarization across the boundary. Finally, the boundary is fused, whereby the first optical fiber and the second optical fiber form a single fiber maintaining orientation of optical polarization.

In adapting this invention to an existing fusion splicer, substantial benefit is realized from the pre-existence of a microprocessor, memory, viewing optics, precision piezoelectric alignment stages, and other elements of the basic apparatus. Additional features to be designed into the platform include the dual rotation stages, dual stepper motors, polarized light projection and receiving optics in the viewing area, and software to operate the system.

The following examples are presented to provide a more complete understanding of the invention. The specific techniques, conditions, materials, proportions, and reported data set forth to illustrate the principles and practice of the invention are exemplary and should not be construed as limiting the scope of the invention.

EXAMPLE 1

Sample polarization-maintaining fibers were examined. The manufacturers included AT&T, Andrew, York, and Hitachi.

Each sample fiber was fixtured in the laboratory and examined under a microscope utilizing transmitted polarized light. Each was rotated, and differences in the lateral light transmission were sought. In each case photographs were taken of the fibers at different rotations to show whether, and to what extent, the rotation state could be distinguished in this lateral view. No power was launched into the fiber cores.

Each fiber plainly showed differences in transmitted intensity during rotation under these conditions. The rotation was most easily visible for the Hitachi, Andrew D, and AT&T fibers. The York fiber was less obvious but still clear. The Andrew E fiber also showed clear and measurable changes in appearance as a function of rotation. The Andrew E fiber is not a "stress-birefringent" polarization-maintaining fiber. Unlike the others, this "form-birefringent" fiber relies on core asymmetry, rather than internal stress regions, to separate the two polarization states in the core. Even this fiber has sufficient residual stress to be aligned using the present invention.

EXAMPLE 2

To measure the actual transverse light intensity versus rotation, linearly polarized light was launched into a Hitachi polarization-maintaining fiber from a HeNe laser. The test end of the fiber was then clamped in a motor-driven rotation stage. The exposed end was passed across a viewing field, with polarized optics and a slit aperture stop. The end of the fiber was then aimed at a detector covered by a polarizing filter. The polarized viewing field comprised a laser, crossed Polaroid filters, and a detector. The outputs of the two detectors were monitored with a storage oscilloscope. In this way the orientation of the polarization axis, as measured by the light received from the end of the fiber through the polarizer, could be compared with the light function (transverse intensity function) created by the transverse viewing optics.

Figure 7:
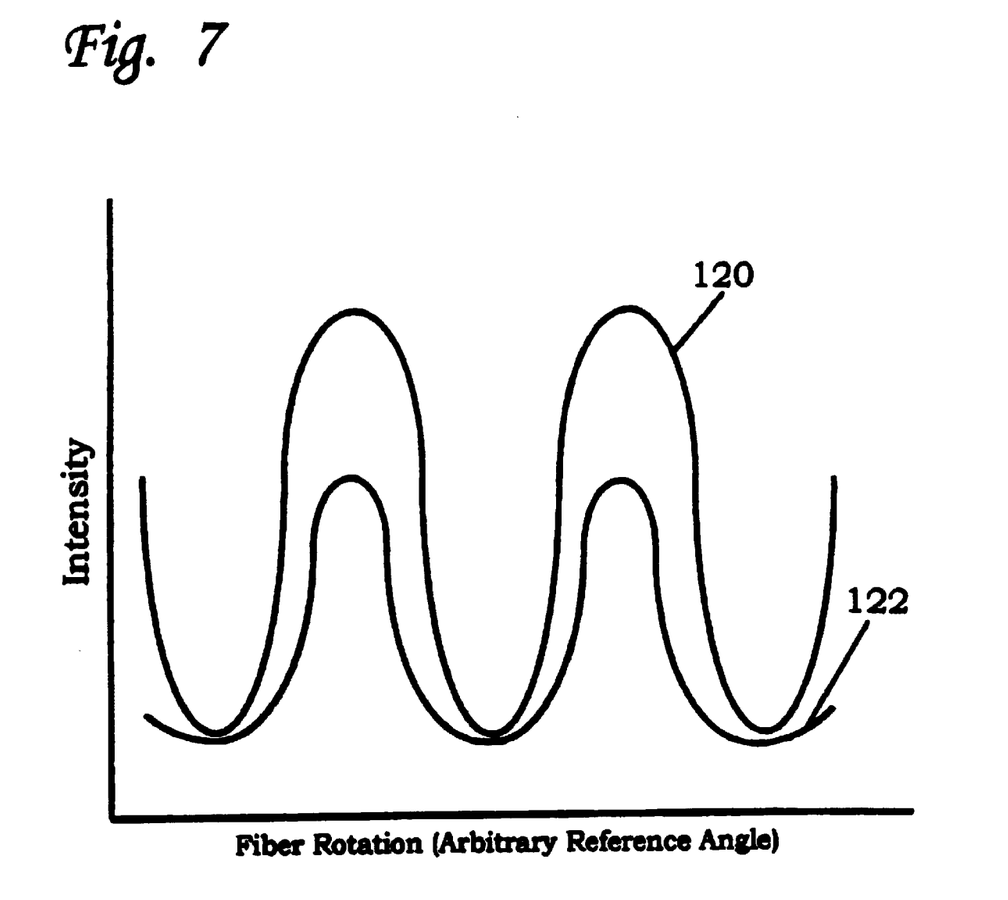
FIG. 7 is a comparative graph of the transverse intensity function and the polarized signal intensity of a sample fiber, showing the correlation.

The peaks of the transverse intensity function corresponded closely with the polarization axes of the fiber. This correspondence survived in spite of the relatively inaccurate alignment of the transmitted light polarizer 120 with the transverse viewing optics axis 122. This is illustrated in FIG. 7.

In addition, it was observed that the Hitachi fiber exhibited substantial core twist, confirming reports in the literature of 2 to 3 degree/cm. This core twist was tested by cutting back the Hitachi fiber and repeating the transverse intensity function measurements. The offsets between the transverse intensity function and the transmitted light function observed in the various trials varied from 5.97 to 12.06 degrees, with an average of 8.38 degrees. If the offset is imputed solely to core twist, the separation between the transverse measurement point and the end of the fiber of 4.5 cm yields an average core twist of 1.86 degree/cm, which agrees well with the values in the literature. If the offset is partially due to polarizer alignment error in the test set-up, then the offset attributable to core twist would be less. In any case, the variation of the twist about the mean is approximately ±3 degrees, or ±0.7 degree/cm, again entirely consistent with the values in the literature. In the present invention, the core twist issue is eliminated by taking the transverse intensity function very close to the fiber tip.

Conclusions

While the method and apparatus of the present invention have been described herein with regard to a particular application, namely, the splicing of polarization-maintaining single mode optical fiber, it has been found that numerous changes and modifications may be made thereto without departing from the spirit of the invention. For example, in certain applications, it may be desirable to install connectors on two polarization-maintaining fibers, so as to permit connections between any two fibers to be made or broken at will. In such applications, as with splicing, the two fibers must be rotationally aligned when connected, so the polarization axes of each must be pre-aligned with a keying feature of its own connector. The two mating connectors are then aligned with each other by a properly designed common receptacle, to further bring their respective fibers into proper mutual alignment. Another application resides in the rotational alignment of a single fiber with a polarized optoelectronic device, such as a laser, a filtered LED, or a filtered receiver. Still another application involves detection of the orientation of the polarization axes at different points in a single fiber. In that application, for instance, a study of the twist of the polarization axes along the length of a fiber may be made without cutting or otherwise harming the fiber. Each of these and other applications derive benefit from methods and means of the present invention, the operation of which is entirely passive to the fiber and is readily carried out without requiring polarized light launch into one end, or polarized light detection from the other end, or special preparation of the measurement point.

Having thus described the invention in rather full detail, it will be understood that such detail need not be strictly adhered to but that further changes and modifications may suggest themselves to one skilled in the art, all falling within the scope of the invention as defined by the subjoined claims.

What is claimed is:

1. Apparatus for aligning two optical fibers, comprising:
   (a) illumination means for projecting polarized light transversely through first and second optical fibers having discrete lengths and observable, internal asymmetric stress;
   (b) polarized light detection means for receiving the light passed transversely through said fibers and producing therefrom an electrically detected signal;
   (c) measuring means for creating first and second transverse intensity functions from variations in said electrically detected signal as said first and second optical fibers are rotated;
   (d) rotation means for rotating each of said first and second optical fibers about an axis through the lengths of said fibers; and
   (e) alignment means for laterally aligning a first end surface of said first optical fiber with a second end surface of said second optical fiber, whereby said first end surface and said second end surface are coincident and form a boundary between said first optical fiber and said second optical fiber.

2. Apparatus as recited by claim 1, wherein each of said optical fibers has characteristic features, and said apparatus further comprises:

(d) correlating means for creating said first and second transverse intensity functions from the outputs of the polarized light detection means and the rotation angles of the rotating means to identify said characteristic features of said fibers; and (e) rotation control means for causing said rotation means to rotate said first optical fiber relative to said second optical fiber until the characteristic features of said first and second fibers are aligned.

3. Apparatus as recited by claim 2, wherein said correlating means further comprises:

(f) memory means for storing said first and second transverse intensity functions; and (g) microprocessor means operative to identify first and second fiber polarization axes from said first and second transverse intensity functions, and the angular difference therebetween.

4. An apparatus, as recited in claim 1, further comprising means joining said first optical fiber to said second optical fiber, whereby said first optical fiber and said second optical fiber are joined as a single fiber and maintain orientation of polarization across said boundary.

5. An apparatus, as recited in claim 3, further comprising joining means for joining said first and second optical fibers as a single fiber in which orientation of polarization is maintained across said boundary.

6. Apparatus for identifying the polarization axis of an optical fiber, comprising:

(a) illumination means for projecting polarized light transversely through said optical fiber, said optical fiber having a discrete length and observable, internal asymmetric stress;

(b) polarized light detection means for receiving the light passed transversely through said fiber and producing therefrom an electrically detected signal;

(c) measuring means for creating a transverse intensity function of said optical fiber from variation in said electrically detected signal as said optical fiber is rotated; and (d) rotation means for rotating said optical fiber about an axis through its length to characterize said transverse intensity function and correlate it with a feature of said fiber.

* * * * *